US011109798B2

(12) United States Patent
Raymann et al.

(10) Patent No.: US 11,109,798 B2
(45) Date of Patent: Sep. 7, 2021

(54) ADJUSTING ALARMS BASED ON SLEEP ONSET LATENCY

(71) Applicant: Apple Inc., Cupertino, CA (US)

(72) Inventors: Roy J. Raymann, Campbell, CA (US); Wren N. Dougherty, San Francisco, CA (US); Divya Nag, Palo Alto, CA (US); Deborah M. Lambert, San Francisco, CA (US); Stephanie Greer, San Francisco, CA (US); Thomas R. Gruber, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/934,983

(22) Filed: Jul. 21, 2020

(65) Prior Publication Data

US 2020/0345298 A1     Nov. 5, 2020

Related U.S. Application Data

(63) Continuation of application No. 16/212,502, filed on Dec. 6, 2018, now Pat. No. 10,758,173, which is a (Continued)

(51) Int. Cl.
*H04M 1/725* (2021.01)
*A61B 5/00* (2006.01)
(Continued)

(52) U.S. Cl.
CPC ......... *A61B 5/4809* (2013.01); *G06Q 10/109* (2013.01); *G08B 21/06* (2013.01);
(Continued)

(58) Field of Classification Search
CPC . A61B 5/4809; A61B 2560/0242; A61B 5/11; A61B 5/0816; A61B 5/02416;
(Continued)

(56) References Cited

U.S. PATENT DOCUMENTS 4,228,806 A * 10/1980 Lidow ................. A61B 5/398
600/544
5,928,133 A * 7/1999 Halyak ................. A61M 21/00
600/26

(Continued)

FOREIGN PATENT DOCUMENTS

EP          2701117 A1    2/2014
WO      2017/058361 A1    4/2017

*Primary Examiner* — Christopher M Brandt
(74) *Attorney, Agent, or Firm* — Invoke

(57) ABSTRACT

In some implementations, a mobile device can adjust an alarm setting based on the sleep onset latency duration detected for a user of the mobile device. For example, sleep onset latency can be the amount of time it takes for the user to fall asleep after the user attempts to go to sleep (e.g., goes to bed). The mobile device can determine when the user intends or attempts to go to sleep based on detected sleep ritual activities. Sleep ritual activities can include those activities a user performs in preparation for sleep. The mobile device can determine when the user is asleep based on detected sleep signals (e.g., biometric data, sounds, etc.). In some implementations, the mobile device can determine recurring patterns of long or short sleep onset latency and present suggestions that might help the user sleep better or feel more rested.

20 Claims, 11 Drawing Sheets

Related U.S. Application Data continuation of application No. 16/038,623, filed on Jul. 18, 2018, now Pat. No. 10,178,972, which is a continuation of application No. 15/792,678, filed on Oct. 24, 2017, now Pat. No. 10,052,061, which is a continuation of application No. 15/590,805, filed on May 9, 2017, now Pat. No. 9,826,930, which is a continuation of application No. 14/871,882, filed on Sep. 30, 2015, now Pat. No. 9,692,874.

(51) Int. Cl.
| | | |
|---|---|---|
| *H04W 4/70* | (2018.01) | |
| *G06Q 10/10* | (2012.01) | |
| *G08B 21/06* | (2006.01) | |
| *H04M 1/72451* | (2021.01) | |
| *H04L 29/08* | (2006.01) | |
| *A61B 5/01* | (2006.01) | |
| *A61B 5/024* | (2006.01) | |
| *A61B 5/08* | (2006.01) | |
| *A61B 5/11* | (2006.01) | |

(52) U.S. Cl.
CPC ........ *H04L 67/22* (2013.01); *H04M 1/72451* (2021.01); *H04W 4/70* (2018.02); *A61B 5/01* (2013.01); *A61B 5/02416* (2013.01); *A61B 5/0816* (2013.01); *A61B 5/11* (2013.01); *A61B 5/4815* (2013.01); *A61B 5/742* (2013.01); *A61B 2560/0242* (2013.01)

(58) Field of Classification Search
CPC ......... A61B 5/01; A61B 5/742; A61B 5/4815; H04W 4/70; G08B 21/06; G06Q 10/109; H04M 1/72566; H04L 67/22
See application file for complete search history.

(56) References Cited

U.S. PATENT DOCUMENTS

| | | | |
|---|---|---|---|
| 6,392,962 B1 * | 5/2002 | Wyatt | G04F 8/08 368/107 |
| 6,547,728 B1 * | 4/2003 | Cornuejols | G04B 25/04 600/300 |
| 6,928,031 B1 * | 8/2005 | Kanevsky | G16H 40/67 368/12 |
| 7,462,150 B1 * | 12/2008 | Bharmi | A61B 5/02405 600/300 |
| 9,692,874 B2 | 6/2017 | Raymann et al. | |
| 9,826,930 B2 | 11/2017 | Raymann et al. | |
| 10,052,061 B2 | 8/2018 | Raymann et al. | |
| 10,178,972 B2 | 1/2019 | Raymann et al. | |
| 2005/0209513 A1 * | 9/2005 | Heruth | A61M 5/1723 600/301 |
| 2006/0019224 A1 | 1/2006 | Behar et al. | |
| 2007/0129622 A1 * | 6/2007 | Bourget | A61B 5/4809 600/382 |
| 2009/0134819 A1 | 5/2009 | Noguchi et al. | |
| 2010/0079294 A1 * | 4/2010 | Rai | A61B 5/18 340/575 |
| 2010/0107184 A1 * | 4/2010 | Shintani | H04N 21/4436 725/10 |
| 2011/0018720 A1 * | 1/2011 | Rai | A61B 5/16 340/575 |
| 2013/0018284 A1 * | 1/2013 | Kahn | A61B 5/681 600/595 |
| 2014/0210626 A1 | 7/2014 | Kresser et al. | |
| 2014/0269223 A1 * | 9/2014 | Mokhnatkina | G04G 21/025 368/73 |
| 2014/0286137 A1 * | 9/2014 | Jeong | G04G 13/023 368/73 |
| 2015/0164238 A1 * | 6/2015 | Benson | A47C 31/00 340/540 |
| 2015/0339792 A1 * | 11/2015 | Emori | A61B 5/4806 705/2 |
| 2016/0005290 A1 * | 1/2016 | Takahashi | A61B 5/024 340/575 |
| 2016/0005291 A1 * | 1/2016 | Takahashi | G04G 13/02 340/575 |
| 2016/0022202 A1 * | 1/2016 | Peterson | G04G 13/023 368/251 |
| 2016/0187856 A1 * | 6/2016 | Vilermo | A61B 5/0816 340/575 |
| 2017/0094046 A1 | 3/2017 | Raymann et al. | |
| 2017/0132946 A1 * | 5/2017 | Kinnunen | A61B 5/4812 |
| 2017/0238864 A1 | 8/2017 | Raymann et al. | |

* cited by examiner

Edit Alarm

| | |
|---|---|
| 4 | |
| 5 | 57 |
| 6 | 58 |
| 7 | 59 AM |
| 8 | 00 PM |
| 9 | 01 |
| 10 | 02 |
| | 03 |

Repeat                Never >

Sound                 Bark >

Auto Adjust           ON

Desired amount of sleep per night:   8 hours

Delete Alarm

| ∨ Sep 2015 | | | | | | |
|---|---|---|---|---|---|---|
| S | M | T | W | T | F | S |
| | | 1 | 2 | 3 | 4 | 5 |
| 6 | 7 | 8 | 9 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | | | |

8:00 AM | Weekly Meeting

11:30 AM | Lunch with Siraj

FIG. 3

ADJUSTING ALARMS BASED ON SLEEP ONSET LATENCY

INCORPORATION BY REFERENCE; DISCLAIMER

Each of the following applications are hereby incorporated by reference: application Ser. No. 16/212,502 filed on Dec. 6, 2018; application Ser. No. 16/038,623 filed on Jul. 18, 2018; application Ser. No. 15/792,678 filed on Oct. 24, 2017; application Ser. No. 15/590,805 filed on May 9, 2017; application Ser. No. 14/871,882 filed on Sep. 30, 2015. The Applicant hereby rescinds any disclaimer of claim scope in the parent application(s) or the prosecution history thereof and advises the USPTO that the claims in this application may be broader than any claim in the parent application(s).

TECHNICAL FIELD

The disclosure generally relates to human sleep detection.

BACKGROUND

Most people require a certain amount of sleep at night to feel well rested the following day. Often, when a person works, the person will set an alarm to wake them up at an appropriate time so that they can arrive at work on time. To get sufficient sleep, the person will go to bed at a time that allows for an appropriate amount of sleep (e.g., 7 hours, 8 hours, etc.). However, most people do not fall asleep right away when they go to bed. So, even if the person goes to bed at an appropriate time to provide 8 hours of sleep, the person often only ends up with 6 or 7 hours of sleep when the alarm goes off in the morning.

SUMMARY

In some implementations, a mobile device can adjust an alarm setting based on the sleep onset latency duration detected for a user of the mobile device. For example, sleep onset latency can be the amount of time it takes for the user to fall asleep after the user attempts to go to sleep (e.g., goes to bed). The mobile device can determine when the user intends or attempts to go to sleep based on detected sleep ritual activities. Sleep ritual activities can include those activities a user performs in preparation for sleep. The mobile device can determine when the user is asleep based on detected sleep signals (e.g., biometric data, sounds, etc.). In some implementations, the mobile device can determine recurring patterns of long or short sleep onset latency and present suggestions that might help the user sleep better or feel more rested.

Particular implementations provide at least the following advantages: the mobile device can help the user feel more rested by automatically adjusting an alarm or suggesting an earlier bedtime based on the determined sleep onset latency to ensure that the user gets enough sleep; the mobile device can automatically determine sleep onset latency using various sensors of the mobile device; the mobile device can automatically identify sleep patterns that may be adversely affecting the user.

Details of one or more implementations are set forth in the accompanying drawings and the description below. Other features, aspects, and potential advantages will be apparent from the description and drawings, and. from the claims.

DESCRIPTION OF DRAWINGS

FIG. 2 illustrates an example graphical user interface for specifying a sleep goal.

FIG. 3 illustrates an example graphical user interface of a calendar application.

Like reference symbols in the various drawings indicate like elements.

DETAILED DESCRIPTION

Overview

Figure 1:
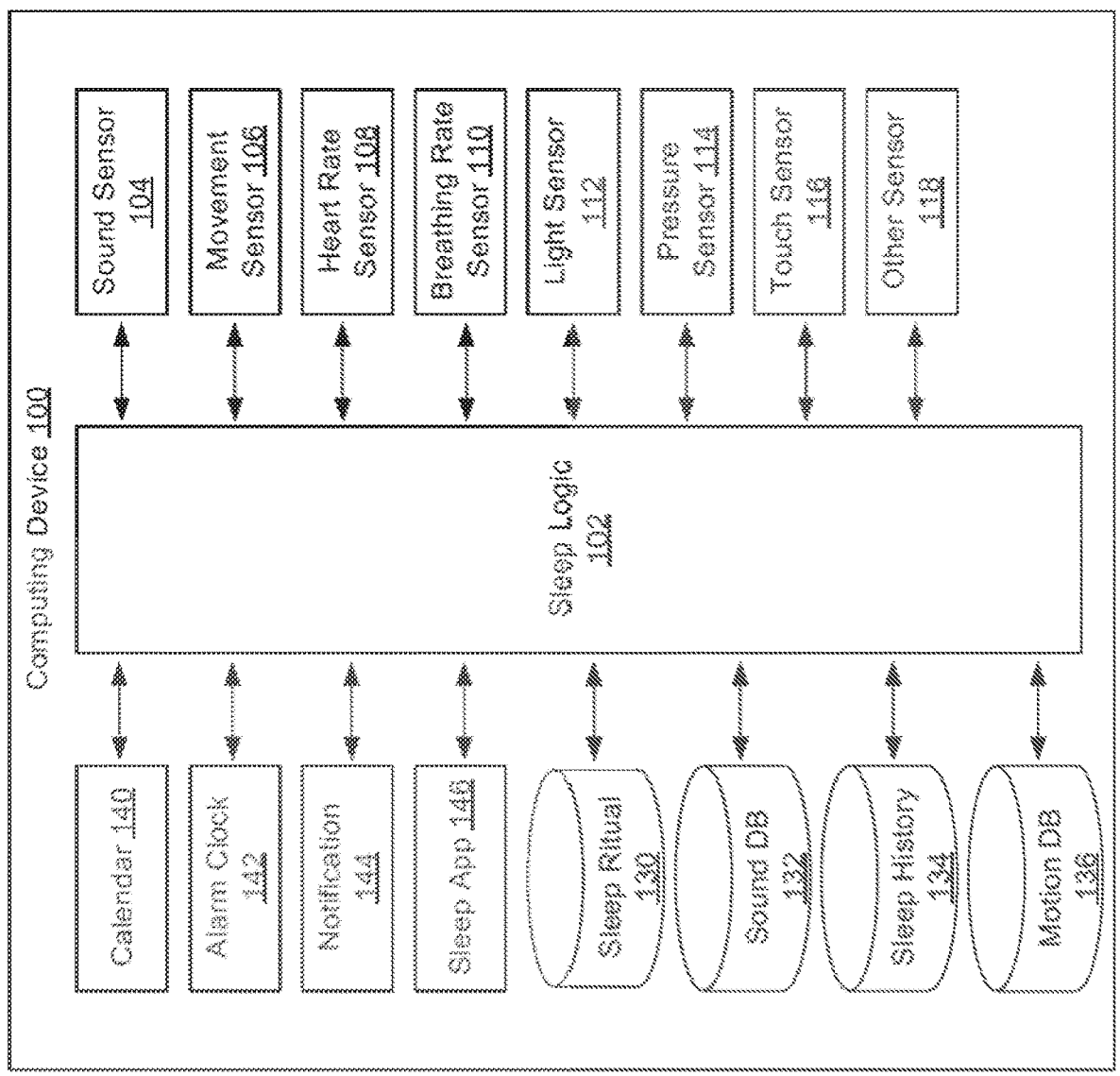
FIG. 1 is a block diagram of an example computing device for adjusting alarms based on sleep onset latency.

FIG. 1 is a block diagram of an example computing device 100 for adjusting alarms based on sleep onset latency. For example, computing device 100 can be a mobile device, such as a smartphone, tablet computer, laptop computer, etc. Computing device 100 can be a wearable device, such as a smart watch, smart eye glasses, smart contacts, etc., for example.

In some implementations, computing device 100 can include sleep logic 102. For example, sleep logic 102 can be an operating system software process (e.g., function, utility, daemon, etc.). Sleep logic 102 can be an independent software process (e.g., a standalone application). Sleep logic 102 can interact with various sensors of computing device 100 to detect sleep signals (e.g., user activities, biometric data, etc.) indicating when the user intends to sleep, when the user actually falls asleep, and when the user wakes up. Sleep logic 102 can use the sleep signals to adjust alarms (e.g., alarm clock, alarms, nap alarms, etc.) on computing device 100 so that the user can get enough sleep and feel rested. For example, sleep logic 102 can use the signals to determine how long it takes for the user to fall asleep (e.g., sleep onset latency) and adjust an alarm (e.g., morning wake up alarm) to allow the user to get sufficient sleep to feel rested.

Detecting Sleep

In some implementations, computing device 100 can detect when the user falls asleep. In some implementations, sleep logic 102 can detect when the user falls asleep based on user input. For example, when the user is using computing device 100 (e.g., using an application, providing user input, etc.), the user is performing a conscious human activity and cannot possibly be sleeping. When the user stops using computing device 100 for a period of time (e.g., 5 hours, 7 hours, etc.), then sleep logic 102 can determine that the user is asleep. Thus, if, for example, the display of computing device 100 is dark (e.g., not illuminated) for a period of time (e.g., at least 7 hours, at least 5 hours, etc.), sleep logic 102 can determine that the user was sleeping during the period of time. Sleep logic 102 can determine the sleep start time based on the time when the sleep period began. For example, if the last user input before the sleep period was at 10:36 pm, then sleep logic 102 can determine that the sleep period began at 10:36 pm. If the screen went dark at 11:16 pm and stayed dark for 7.5 hours, then sleep logic 102 can determine that the sleep period began at 11:16 pm, for example.

In some implementations, sleep logic 102 can detect when the user falls asleep based on sensor data. For example, computing device 100 can include various sensors that can detect environmental and/or biometric signals that can be used to determine when the user is sleeping. Sleep logic 102 can detect sleep based on a single signal (e.g., heartrate) or a combination of signals (e.g., heartrate, breathing, movement, etc.). For example, sleep logic 102 can use multiple signals to improve the probability that the sleep determination is correct. When the detected signals correspond to sleep (as described below), sleep logic 102 can determine that the user is asleep. For example, when the detected signals correspond to sleep for a period of time (e.g., at least 5 hours, at least 6 hours, etc.), then sleep logic 102 can determine that the user is asleep. If a detected signal corresponds to the user being awake (e.g., conscious, active, etc.), then sleep logic 102 can determine that the user is awake, as described further below.

In some implementations, computing device 100 can include sound sensor 104 (e.g., a microphone) that can detect sounds near computing device 100. In some implementations, sound sensor 104 can detect sleep sounds. For example, sleep logic 102 can initially determine that the user is sleeping based on the absence of user input, as described above. Sound sensor 104 can collect sleep sounds while the user is sleeping. (e.g., snoring, slow breathing, bed sounds generated when the user moves in the bed, etc.). Sleep logic 102 can store the collected sleep sounds in sound database 132. When sleep logic 102 later detects similar sleep sounds, sleep logic 102 can analyze the sleep sounds and determine that the sleep sounds correspond to the user sleeping by comparing the detected sleep sounds to the sleep sounds in sound database 132.

In some implementations, computing device 100 can include movement sensor 106. For example, movement sensor 106 can be an accelerometer. Movement sensor 106 can detect when computing device 100 is moving, for example. When the user of computing device 100 is holding or wearing computing device 100 and the user moves, movement sensor 106 can detect the movement and sleep logic 102 can determine that the user is awake. When movement sensor 106 detects very little movement (e.g., below a threshold frequency, or threshold magnitude), then sleep logic 102 can determine that the user is asleep.

In some implementations computing device 100 can include heart rate sensor 108. For example, heart rate sensor 110 can be a motion sensor. For example, the motion sensor can be worn near the heart or on the wrist to detect motion corresponding to the user's pulse. Heart rate sensor 110 can be a microphone. For example, the microphone can be worn on the wrist near the radial artery to detect sounds corresponding to the user's pulse. Heart rate sensor 110 can be a photoplethysmogram (PPG) sensor, such as a pulse oximeter camera, or other optical sensor. Heart rate sensor 110 can optically obtain a plethysmogram by illuminating the skin and measuring changes in light absorption to detect the user's pulse. Sleep logic 102 can use the pulse data generated by heart rate sensor 110 to determine a heart rate for the user. Sleep logic 102 can use the pulse data generated by heart rate sensor 108 to determine the variability in the user's pulse. For example, pulse or heart rate variability decreases as the user transitions from a wake state to a sleep state. Sleep logic 102 can determine that the user is sleeping when the user's heart rate and/or heart rate variability is below respective threshold values. Sleep logic 102 can determine that the user is awake when the user's heart rate and/or heart rate variability are above respective threshold values.

In some implementations, computing device 100 can include breathing rate sensor 110. For example, breathing rate sensor 110 can be a microphone. For example, the microphone can detect sounds corresponding to breaths taken by the user. Breathing rate sensor 110 can be a photoplethysmogram (PPG) sensor such as a pulse oximeter, camera, or other optical sensor. Breathing rate sensor 110 can optically obtain a plethysmogram by illuminating the skin and measuring changes in light absorption to detect when the user takes a breath. Sleep logic 102 can use the breathing rate data generated by breathing rate sensor 110 to determine a breathing rate (e.g., frequency of breaths), breathing rate variability, and/or breathing amplitude (e.g., how big or deep the breaths are for the user. Sleep logic 102 can determine that the user is sleeping when the user's breathing rate, breathing rate variability, and/or breathing amplitude are below respective threshold values. Sleep logic 102 can determine that the user is awake when the user's breathing rate, breathing rate variability, and/or breathing amplitude are above respective threshold values. For example, slow, regular breaths can indicate that the user is sleeping while faster, inconsistent breathing can indicate that the user is awake.

In some implementations, computing device 100 can include light sensor 112. For example, light sensor 112 can be a photoresistor that detects the light intensity of the environment around computing device 100. Sleep logic 102 can use the light intensity data generated by light sensor 112 to determine whether the user is sleeping. For example, humans usually enjoy sleeping in a dark environment. Thus, when light sensor 112 detects that the light intensity is above a threshold intensity value, sleep logic 102 can determine that the user is awake. When light sensor 112 detects that the light intensity is below the threshold value, sleep logic 102 can determine that the user is sleeping.

In some implementations, computing device 100 can include pressure sensor 114. For example, pressure sensor 114 can be incorporated into or behind a touch sensitive display of computing device 100. A user can touch and apply pressure to the touch sensitive display and pressure sensor 114 can determine the amount of pressure being applied to the touch sensitive display. To determine the start of sleep, the user can be prompted to apply and hold pressure to the touch sensitive display. When the user falls asleep, the user will not be able to continue applying pressure to the display. Sleep logic 102 can receive pressure data from pressure sensor 114, determine the amount of pressure being applied to the display by the user has decreased (e.g., below some pressure value), and determine that the user is asleep based on the decrease in pressure.

In sonic implementations, computing device 100 can include touch sensor 116. For example, touch sensor 116 can be a touch sensitive display, a button, or some other device that is responsive to the user's touch. Sleep logic 102 can use the touch sensor data generated by touch sensor 116 to determine if the user is awake or asleep. For example, when touch sensor 116 detects that the user has touched computing device 100 (e.g., the touch sensitive display, button, etc.), then sleep logic 102 can determine that the user is awake. When touch sensor 116 does not detect the user touching computing device 100 for a period of time (e.g., 4 hours, 6 hours, etc.), then sleep logic 102 can determine that the user is asleep.

In some implementations, computing device 100 can include other sensors 118. For example, other sensors 118 can include a temperature sensor, a location sensor, or any other sensor that can generate data that can be used to inform the sleep determination. For example, the temperature sensor can detect the heat of the user's skin. Typically, skin temperature (e.g., surface temperature) of the human body increases while sleeping. Thus, sleep logic 102 can determine that the user is sleeping when the skin temperature data generated by the temperature sensor indicates an increase in the user's body temperature above a threshold temperature. When other sensors 118 is a location sensor, for example, sleep logic 102 can determine that the user is sleeping when the location of computing device 100 is the user's home or at some other place where the user typically sleeps. For example, sleep logic 102 may determine that the user is still awake when the location of computing device 100 is the user's place of business.

In some implementations, sleep logic 102 can determine when the user is awake using the sensors described above. For example, the various sensors can detect conscious human activity and sleep logic 102 can determine that the user is awake based on the detected activity. For example, sleep logic 102 can receive sensor data that indicates conscious movement, talking, increased heart rate, increased breathing rate, increased lighting, and/or use of computing device 100 (e.g., touch input) and determine that the user is awake based on the sensor data. Sleep logic 102 can determine the wake time based on when the first sensor detected conscious human activity. For example, the wake time can correspond to the time when a sensor first detected conscious movement, talking; increased heart rate, increased breathing rate, increased lighting, and/or use of computing device 100 (e.g., touch input).

In some implementations, the sleep start time and sleep end time (wake time) can be used to determine the sleep period. For example, if the sleep start time is 11 pm and the sleep end time is 6 am, then the sleep period (duration) is 7 hours (e.g., 6 am-11 pm=7 hours). In some implementations, sleep logic 102 can store sleep the sleep start time, sleep end time, and/or sleep duration in sleep history database 134. For example, each record in sleep history database 134 can include sleep data for an instance of sleep. The sleep data can include sleep start time, sleep end time, sleep period duration, and sensor data collected while the user is sleeping, as described above. The sensor data can be used to confirm sleep state when determining whether the user is sleeping by comparing the stored sensor data representing the user's sleep state to current sensor data representing the user's current unknown state.

In some implementations, sleep logic 102 can predict future sleep periods. For example, sleep logic 102 can analyze the sleep history data in sleep history database 134 to determine when the user usually sleeps. For example, if the user typically (e.g., historically has a pattern) sleeps between 11 pm, and 7 am, then sleep logic 102 can predict that the user will go to sleep at 11 pm on the current day and/or future days.

Determining the Sleep Ritual

In some implementations, sleep logic 102 can determine the user's sleep ritual. For example, humans are creatures of habit. Most people have a specific set of activities that they perform before going to bed every night. For example, a user of computing device 100 may take the dog out, lock the front door, shut the window blinds, exercise, take a shower, and/or brush her teeth. These activities may not be done in the exact same order every night. The user may not perform every one of these activities every night. However, each night the user will perform at least some (e.g., a subset) of these activities as part of the user's sleep ritual before she goes to bed. For example, if a user performs a particular activity at least a threshold number of nights (e.g., 5, 6, at least 50%, etc.) per week, then sleep logic 120 can determine that the particular activity is a sleep ritual activity. These sleep ritual activities can be used to infer the user's intent to go to sleep.

In some implementations, sleep logic 102 can monitor sensor data before the user goes to sleep to determine the user's sleep ritual. For example, after sleep logic 102 determines the user's sleep patterns, as described above, sleep logic 102 can monitor the environment of computing device 100 to determine the user's activities right before the user is predicted to go to sleep. If sleep logic 102, for example, predicts that the user will go to sleep at 10 pm, for example, sleep logic 102 can turn on the sensors of computing device 100 before the user is predicted to go to sleep (e.g., 5 hour before, 1 hour before, 9:30 pm, etc.) to monitor or detect the user's bedtime activities (e.g., sleep ritual).

In some implementations, sleep logic 120 can monitor the environment of computing device 100 to determine the user's activities all the time or on regular intervals (e.g., every 2 minutes, every 5 minutes, etc.) throughout the day to detect and identify the user's activities. When sleep logic 120 determines that the user has gone to sleep, sleep logic 120 can analyze the user's activities to determine which activities were performed in a time period (e.g., 30 minutes, 1 hour, etc.) before the user went to sleep.

In some implementations, sleep logic 102 can identify sleep ritual activities using sound data generated by sound sensor 104. For example, various activities performed by the user as the user is preparing to go to sleep may generate noise or sounds that are detectable by sound sensor 104 and/or identifiable by sleep logic 102. Sleep logic 102, for example, can obtain sound samples (e.g., sound fingerprints) from a network resource (not shown) that have been mapped to corresponding human activities that are known to have generated the sampled sounds. The sound samples can include the sound of someone brushing their teeth, adjusting window blinds, opening and closing doors, taking a shower, or any other activity that generates an identifiable or unique sound. The mapping of sounds to activities can be stored in sound database 132, for example. Thus, when the user brushes her teeth, the sound of the brushing can be detected by sound sensor 104 (e.g., microphone), and can be compared to the sounds in sound database 132 by sleep logic 102 to determine that the detected sound corresponds to the user brushing her teeth. After sleep logic 102 identifies the sound of the user brushing her teeth, the user's tooth brushing activity can be added to the user's sleep ritual activities stored in sleep ritual database 130, for example. Similarly, sound sensor 104 can detect and sleep logic 102 can identify sounds related to exercising, showering, closing window blinds, opening and closing doors, taking a dog outside, filling a glass with water, using the toilet, and/or any other sleep ritual activity. After a sleep ritual activity has been identified, sleep logic 102 can add the sleep ritual activity to sleep ritual database 130.

In some implementations, sleep logic 102 can identify sleep ritual activities using movement data generated by movement sensor 106. For example, various activities performed by the user as the user is preparing to go to sleep may generate motion or vibrations that are detectable by movement sensor 106 and/or identifiable by sleep logic 102. Sleep logic 102 can, for example, obtain motion samples (e.g., motion fingerprints, patterns of motion) from a network resource (not shown) that have been mapped to corresponding activities that are known to have generated the sampled motion. The motion samples can include the motion of someone brushing their teeth (e.g., when. wearing a smart watch), walking or exercising, or any other activity that generates motion or movement. The mapping of motion to activities can be stored in motion database 136, for example. Thus, when the user exercises before bed, the motion of the exercise can be detected by movement sensor 106 (e.g., accelerometer), and can be compared to the motion samples in motion database 136 by sleep logic 102 to determine that the detected motion corresponds to the user exercising. After sleep logic 102 identifies the motion of the user exercising, the user's exercise activity can be added to the user's sleep ritual activities stored in sleep ritual database 130. Similarly, movement sensor 106 can detect and sleep logic 102 can identify motion related to tooth brushing, and/or any other sleep ritual activity. After a sleep ritual activity has been identified, sleep logic 102 can add the sleep ritual activity to sleep ritual database 130.

In some implementations, sleep logic 102 can identify sleep ritual activities using light intensity data generated by light sensor 112. For example, humans normally like to sleep in a dark room. Thus, darkening the user's environment by drawing window shades or turning off a light can be part of the user's sleep ritual. When the user darkens the room before the predicted bedtime, light sensor 112 can detect the change in ambient light intensity and generate ambient light intensity data reflecting the change. Sleep logic 102 can analyze the light intensity data, determine that the ambient light intensity has been lowered, and determine that the user has darkened the room. Sleep logic 102 can store the darken room activity is sleep ritual database 130 as an activity that is part of the user's sleep ritual.

In some implementations, sleep logic 102 can identify sleep ritual activities based on application usage. For example, the user may have a habit of using specific software applications installed on computing device 100 immediately before going to bed. The user can check calendar application 140. The user can set a wake up alarm using alarm clock application 142. The user can use social media applications, news applications, a game application, an e-book reader application, and/or other applications before going to sleep. Sleep logic 102 can monitor application usage before the predicted sleep time (e.g., 1 hour before, 0.5 hour before, etc.) and determine which applications the user uses before the user's predicted sleep time. Sleep logic 102 can store the detected application use activities as sleep ritual activities in sleep ritual database 130.

Determining Intent to Sleep

In some implementations, sleep logic 102 can determine the start of sleep onset latency by determining that the user intends to sleep at a particular time. For example, a user's sleep onset latency is the period or duration of time that elapses starting when the user intends to go to sleep and ending when the user actually falls asleep.

In some implementations, the user's intent to sleep can be determined based on detecting the user has performed the user's sleep ritual. For example, sleep logic 102 can monitor the activities of the user before the user's predicted sleep period using the sensors of computing device 100, as described above. Sleep logic 102 can identify the user's activities based on the sensor data, as described above, and compare the activities to the activities stored in sleep ritual database 130 to determine if the detected activity is part of the user's sleep ritual. Sleep logic 102 can determine that the user's sleep ritual was performed by the user when sleep logic 102 determines that a threshold number of the sleep ritual activities identified in sleep database 130 were performed. For example, sleep logic 102 can determine that the user is performing the user's sleep ritual when a minimum number (e.g., three or more) of the sleep ritual activities were performed in a short period of time (e.g., within 15 minutes, within 30 minutes, etc.). Sleep logic can determine that the user is performing the user's sleep ritual when a portion (e.g., greater than 30%, greater than 50%, etc.) of the sleep ritual activities were performed by the user in a short period of time.

In some implementations, sleep logic 102 can determine the start of the user's sleep onset latency based on the time when the last of the user's sleep ritual activities is performed. If the user's sleep ritual (as indicated by the activities in sleep ritual database 130) includes the activities shower, brush teeth, darken the room, and set the wake up alarm for the next day, then, when the last of these activities is detected by the sensors of computing device 100, sleep logic 102 can determine that the user intends to sleep. For example, if darkening the mom is the last of the sleep ritual activities performed by the user and detected by light sensor 112 of computing device 100, then sleep logic 102 can determine the start of the user's sleep onset latency to be the time at which darkening the room was detected. If setting the alarm (e.g., using an alarm clock application) is the last of the sleep ritual activities detected by computing device 100, then sleep logic 102 can determine the start of the user's sleep onset latency to be the time at which the user set the alarm.

In some implementations, sleep logic 102 can determine the start of the user's sleep onset latency based on heart rate data generated by heart rate sensor 108. For example, the user's heart rate may decrease in steps: first as a user prepares to sleep and again when the user is actually asleep. Thus, sleep logic 102 can include two heart rate thresholds: a first heart rate threshold for determining intent to sleep or the start of sleep onset latency, and a second heart rate threshold lower than the first heart rate threshold for determining when the user is sleeping. Heart rate sensor 108 can detect the user's heart rate, as described above, and send the heart rate data to sleep logic 102. Sleep logic 102 can compare the user's heart rate to the first and second heart rate thresholds. For example, if the user's heart rate is below the first heart rate threshold and above the second heart rate threshold, the user is preparing to sleep and has begun the sleep onset latency period. If the user's heart rate is below the second heart rate threshold, the user is sleeping. Thus, sleep logic 102 can determine the start of sleep onset latency when the user's heartrate drops below the first heart rate threshold. Sleep logic 102 can determine the end of sleep onset latency and the beginning of sleep when the user's heartrate drops below the second heart rate threshold.

Similarly, the user's heart rate variability may decrease in steps: first when the user is awake and resting, second when the user intends to sleep, and third when the user is asleep. Thus, sleep logic 102 can include two heart rate variability thresholds for determining sleep onset latency: a first variability threshold for determining intent to sleep or the start of sleep onset latency, and a second variability threshold lower than the first variability threshold for determining when the user is sleeping. Heart rate sensor 108 can detect the user's heart rate, as described above, and send the heart rate data to sleep logic 102. Sleep logic 102 can compare the user's heart rate variability to the first and second variability thresholds. For example, if the user's heart rate variability is below the first variability threshold and above the second variability threshold, the user is preparing to sleep and has begun the sleep onset latency period. If the user's heart rate variability is below the second variability threshold, the user is sleeping. Thus, sleep logic 102 can determine the start of sleep onset latency when the user's heart rate. variability drops below the first heart rate threshold. Sleep logic 102 can determine the end of sleep onset latency and the beginning of sleep when the user's heart rate variability drops below the second variability threshold.

In some implementations, sleep logic 102 can determine the start of the user's sleep onset latency based on breathing rate data generated by breathing rate sensor 110. For example, the user's breathing rate may decrease in steps: first as a user prepares to sleep and again when the user is actually asleep. Thus, sleep logic 102 can include two breathing rate thresholds: a first breathing rate threshold for determining intent to sleep or the start of sleep onset latency, and. a second breathing rate threshold lower than the first breathing rate threshold for determining when the user is sleeping. Breathing rate sensor 108 can detect the user's breathing rate, as described above, and send the breathing rate data to sleep logic 102. Sleep logic 102 can compare the user's breathing rate to the first and second breathing rate thresholds. For example, if the user's breathing rate is below the first breathing rate threshold and above the second breathing rate threshold, the user is preparing to sleep and has begun the sleep onset latency period. If the user's breathing rate is below the second breathing rate threshold, the user is sleeping. Thus, sleep logic 102 can determine the start of sleep onset latency when the user's breathing drops below the first breathing rate threshold. Sleep logic 102 can determine the end of sleep onset latency and the beginning of sleep when the user's breathing drops below the second breathing rate threshold.

Similarly, the user's breathing rate variability may decrease in steps: first as a user prepares to sleep and again when the user is actually asleep. Thus, sleep logic 102 can include two breathing variability thresholds: a first variability threshold for determining intent to sleep or the start of sleep onset latency, and a second variability threshold lower than the first variability threshold for determining when the user is sleeping. Breathing rate sensor 108 can detect the user's breathing rate, as described above, and send the breathing rate data to sleep logic 102. Sleep logic 102 can compare the user's breathing rate variability to the first and second variability thresholds. For example, if the user's breathing rate variability is below the first variability threshold and above the second variability threshold, the user is preparing to sleep and has begun the sleep onset latency period. If the user's breathing rate variability is below the second variability threshold, the user is sleeping. Thus, sleep logic 102 can determine the start of sleep onset latency when the user's breathing rate variability drops below the first variability threshold. Sleep logic 102 can determine the end of sleep onset latency and the beginning of sleep when the user's breathing rate variability drops below the second variability threshold. Similar thresholding logic can be used to determine sleep onset latency based on breathing amplitude, as described above.

In some implementations, sleep logic 102 can determine the start of the user's sleep onset latency based on user input detected by pressure sensor 114. For example, sleep logic 102 can use pressure sensor 114 to determine when the user intends to sleep and the start of sleep. Sleep logic 102 (or sleep application 146) can present a graphical user interface on a touch sensitive display of computing device 100. The graphical user interface can ask the user to apply and hold pressure on the display when the user intends to sleep. The pressure applied by the user can be detected by pressure sensor 114. Pressure sensor 114 can detect a high level of pressure initially. The amount of pressure detected by pressure sensor 114 will be reduced as the user falls asleep until little or no pressure is detected when the user is asleep. The pressure data generated by pressure sensor 114 can be analyzed by sleep logic 102 to determine when the user initially applied pressure (e.g., corresponding to the users intent to sleep) and when the user applied the least amount of pressure after the initial pressure was applied (e.g., corresponding to when the user fell asleep) to determine the start and end of the sleep onset latency period.

In some implementations, sleep logic 102 can determine the start of the user's sleep onset latency based on user input detected by touch sensor 116. For example, sleep logic 102 and/or sleep application 146 can provide a graphical user interface that allows the user to indicate that the user intends to go to sleep. The user can, for example, touch a button or graphical user interface element on a touch sensitive display to indicate the user's intent to go to sleep. Touch sensor 116 can detect the touch input and sleep logic 102 can determine the start of the sleep onset latency period based on when the touch input was received.

In some implementations, sleep logic 102 can determine the sleep onset latency duration based on the sleep onset latency start time and the sleep onset latency end time (e.g., sleep start time). For example, sleep onset latency can be the duration of time that passes between when the user intends to sleep and when the user actually falls asleep. The beginning of sleep onset latency can be determined based on sleep ritual information, biometric data (e.g., breathing rate, heart rate, etc.), and/or user input, as described above. The end of sleep onset latency and the beginning of sleep can be determined based on biometric signals (e.g., breathing rate, heart rate, breathing sounds, movement, etc.) as described above. Upon detecting that the user has fallen asleep, sleep logic 102 can determine the duration of the sleep onset latency based on the amount of time between the sleep onset latency start time and the sleep onset latency end time. The sleep onset latency duration can be stored in sleep history database 134, described above. For example, the determined sleep onset latency duration can be included in a sleep record corresponding to the current sleep instance in sleep history database 134.

Using Sleep Onset Latency to Min & Alarms

In some implementations, sleep logic 102 can use the determined sleep onset latency to adjust alarm clock settings on computing device 100. For example, upon determining the sleep onset latency duration, sleep logic 102 can obtain alarm clock settings information from alarm clock application 142. The alarm clock settings information can, for example, describe a time the following morning when the alarm clock will generate a sound to wake the user from sleeping. Sleep logic 102 can adjust the alarm clock settings based on the sleep onset latency duration to change the time when the alarm will sound to allow the user more time to sleep. For example, if the wake alarm is set for 7 am and. the user's sleep onset latency duration is 45 minutes, sleep logic 102 can use an application programming interface (AK) of alarm clock application 142 to adjust the wake alarm so that the alarm sounds and wakes the user at 7:45 am. For example, sleep logic 102 can adjust the wake alarm time by adding the sleep latency duration of 45 minutes to the scheduled alarm time of 7 am.

In some implementations, sleep logic 102 can determine whether to adjust the alarm clock settings based on calendar data. For example, when adjusting an alarm time in alarm clock application 142, sleep logic 102 can determine whether adjusting the alarm time will conflict with a calendar event scheduled in calendar application 140. Sleep logic 102 can obtain the calendar event information from calendar application 140, for example, and determine if the calendar event information indicates that there is a calendar event scheduled that should prevent adjusting the alarm lime. Continuing the example above, if the calendar event data indicates that the user has scheduled a meeting at 7:30 am then sleep logic 102 will not change the alarm time to 7:45 am because changing the alarm time would cause the user to miss the 7:30 meeting. However, if the calendar event data indicates that the user has a meeting scheduled for 9:00 am, sleep logic 102 can change the alarm time to 7:45 because the user will still be able to make the scheduled meeting.

In some implementations, sleep logic 102 can determine whether to adjust the alarm clock settings based on an estimated travel time to a meeting scheduled in calendar application 140. For example, when determining whether to adjust an alarm time in alarm clock application 142, sleep logic 102 can determine whether the new alarm time generated based on the sleep onset latency duration will allow enough time for the user to travel to a location associated with a calendar event scheduled in calendar application 140. Sleep logic 102 can obtain the calendar event information from calendar application 140, for example, and determine if the calendar event information indicates that there is a calendar event scheduled after the new alarm time. Sleep logic 102 can determine the location of the scheduled calendar event (e.g., location of a meeting) and estimate the travel time from the user's sleep location to the calendar event location. If the amount of time between the new alarm time and the calendar event time does not allow for enough time to travel to the meeting location, sleep logic 102 will not change the scheduled alarm time to the new alarm time. Continuing the example above, if the calendar event data indicates that the user has scheduled a meeting at 8:30 am and the travel time between the user's sleep location (e.g., the user's home) is 1 hour, then sleep logic 102 will not change the alarm time to 7:45 am because changing the alarm time would cause the user to miss the 8:30 meeting (e.g., the user would arrive at the meeting at 8:45 am). However, if the calendar event data indicates that the user has a meeting scheduled for 9:00 am, sleep logic 102 can change the alarm time to 7:45 because the user will still be able to make the scheduled meeting (e.g., the user has enough time to travel 1 hour to the meeting).

In some implementations, sleep logic 102 can determine whether to adjust the alarm clock settings based on a morning ritual duration. For example, when determining whether to adjust a scheduled alarm time in alarm clock application 142, sleep logic 102 can determine whether the new alarm time generated based on the user's sleep onset latency will allow enough time for the user to perform the user's morning ritual and still attend the calendar event scheduled in calendar application 140. For example, the user's morning ritual includes activities that the user performs when the user wakes up in the morning to get ready to leave the user's house (e.g., get ready for work). The user's morning ritual can be determined similarly to the user's bedtime ritual (e.g., by using sensor data to identify morning activities after the user wakes). Sleep logic 102 can estimate the duration of the morning ritual based on a start time corresponding to when the user wakes (e.g., as detected by the user's use of computing device 100) and an end time corresponding to the last morning ritual activity performed. For example, sleep logic 102 can determine the duration of the morning ritual by determining the start time based on the user's use of computing device 100 and the end time based on when the user leaves the sleep location (e.g., the user's house). Sleep logic 102 can determine that the user has left the sleeping location based on location data (e.g., satellite location data, cellular location data, Wi-Fi location data, etc.) generated or obtained by computing device 100, for example. Sleep logic 102 can calculate the duration of the morning ritual by calculating the amount of time between the start time and the end time of the morning ritual.

Sleep logic 102 can obtain the calendar event information from calendar application 140, for example, and determine if the calendar event information indicates that there is a calendar event scheduled after the new alarm time. If the amount of time between the new alarm time and the calendar event time does not allow for enough time for the user to perform the user's morning ritual, sleep logic 102 will not change the scheduled alarm time to the new alarm time. Continuing the example above, if the calendar event data indicates that the user has scheduled a meeting at 8:30 am and the amount of time the user needs to perform the user's morning ritual is 1 hour, then sleep logic 102 will not change the alarm time to 7:45 am because changing the alarm tune would cause the user to miss the 8:30 meeting (e.g., the users morning ritual would. last until 8:45 am). However, if the calendar event data indicates that the user has a meeting scheduled for 9:00 am, sleep logic 102 can change the alarm time to 7:45 because the user will still be able to perform the user's morning ritual and attend the scheduled meeting (e.g., the user has enough time to get ready for the meeting).

In some implementations, sleep logic 102 can determine whether to adjust the alarm clock settings based on the morning ritual duration and the amount of time needed to travel to a scheduled meeting. Continuing the example above, if the calendar event data indicates that the user has scheduled a meeting at 8:30 am and the amount of time the user needs to perform the user's morning ritual (e.g. 0.5 hour) and travel (e.g., 1 hour) to the meeting location is 1.5 hours, then sleep logic 102 will not change the alarm time to 7:45 am because changing the alarm time would cause the user to miss the 8:30 meeting (e.g., the users would not arrive at the meeting until 9:15 am). However, if the calendar event data indicates that the user has a meeting scheduled for 9:30 am, sleep logic 102 can change the alarm time to 7:45 because the user will still be able to perform the user's morning ritual and travel to the scheduled meeting location in time to attend the scheduled meeting.

In some implementations, sleep logic 102 can determine whether to adjust the alarm clock settings based on a user's sleep goal. For example, the user of computing device 100 can specify a number of hours that the user would like to sleep each night. Sleep logic 102 can adjust the alarm clock settings based on the sleep goal in the same way as sleep logic 102 adjusts the alarm clock settings based on the sleep onset latency duration, as described above. For example, sleep logic 102 can determine when the user falls asleep. Sleep logic 102 can determine when the user should wake up based when the user fall asleep and the sleep goal. Sleep logic 102 can determine whether to adjust a scheduled alarm time to allow the user to sleep the number of hours specified by the user's sleep goal by determining whether the a new sleep time generated based on the user's sleep goal will cause the user to miss a scheduled meeting, a described above. Sleep logic 102 can determine whether the scheduled alarm time can be adjusted to accommodate the user's sleep goal based on travel time and/or the duration of the user's morning ritual to, for example.

In some implementations, sleep logic 102 can suggest an adjustment to the user's sleep routine when a scheduled alarm time should not be adjusted based on the user's sleep onset latency. For example, when sleep logic 102 determines that the user has a sleep onset latency duration of 30 minutes and determines that the scheduled alarm time cannot be adjusted, as described above, sleep logic 102 can cause notification process 144 to present a message on the display of computing device 100 that suggests an earlier bedtime to the user. For example, sleep logic 102 can send the message to notification process 144 and notification process 144 can present the message in a notification on the display of computing device 100. Notification process 144 can be a standalone application or a process or function of the operating system of computing device 100, for example.

FIG. 2 illustrates an example graphical user interface 200 for specifying a sleep goal. For example, graphical user interface (GUI) 200 can be a GUI of alarm clock application 142. GUI 200 can be presented on a display of computing device 100. GUI 200 can present graphical elements 202 that a user can select or manipulate to specify a time (e.g., 7:00 am) at which an alarm should be presented by alarm clock application 142 on computing device 100. For example, the alarm can be presented as a sound, a vibration, and/or a graphical notification presented by computing device 100. GUI 200 can present graphical element 204 that a user can select to turn on or off the automatic alarm adjustment features described above. For example, the user can select graphical element 204 to enable or disable automatic adjustment of the alarm time specified using graphical elements 202 based on the user's sleep onset latency duration and/or sleep goal. GUI 200 can present graphical element 206 that allows a user to specify an amount of time for the user's sleep goal. For example, the user can type a number into graphical element 206 to specify the user's sleep goal.

FIG. 3 illustrates an example graphical user interface 300 of a calendar application. For example GUI 300 can be a graphical user interface of calendar application 140. GUI 300 can be presented on a display of computing device 100. GUI 300 can represent calendar events (e.g., meetings) that are scheduled in calendar application 140. For example, GUI 300 can present information related to meeting 302 scheduled at 8:00 am. In some implementations, sleep logic 102 can determine whether to adjust alarm time specified using graphical element 202 of FIG. 2 for the user's sleep onset latency based on whether the adjusted alarm time would cause the user to miss meeting 302 scheduled in calendar application 140. Sleep logic 102 can determine whether the user would miss meeting 302 based on the sleep onset latency adjustment, travel time, and/or the duration of the user's morning ritual, as described above.

Figure 4:
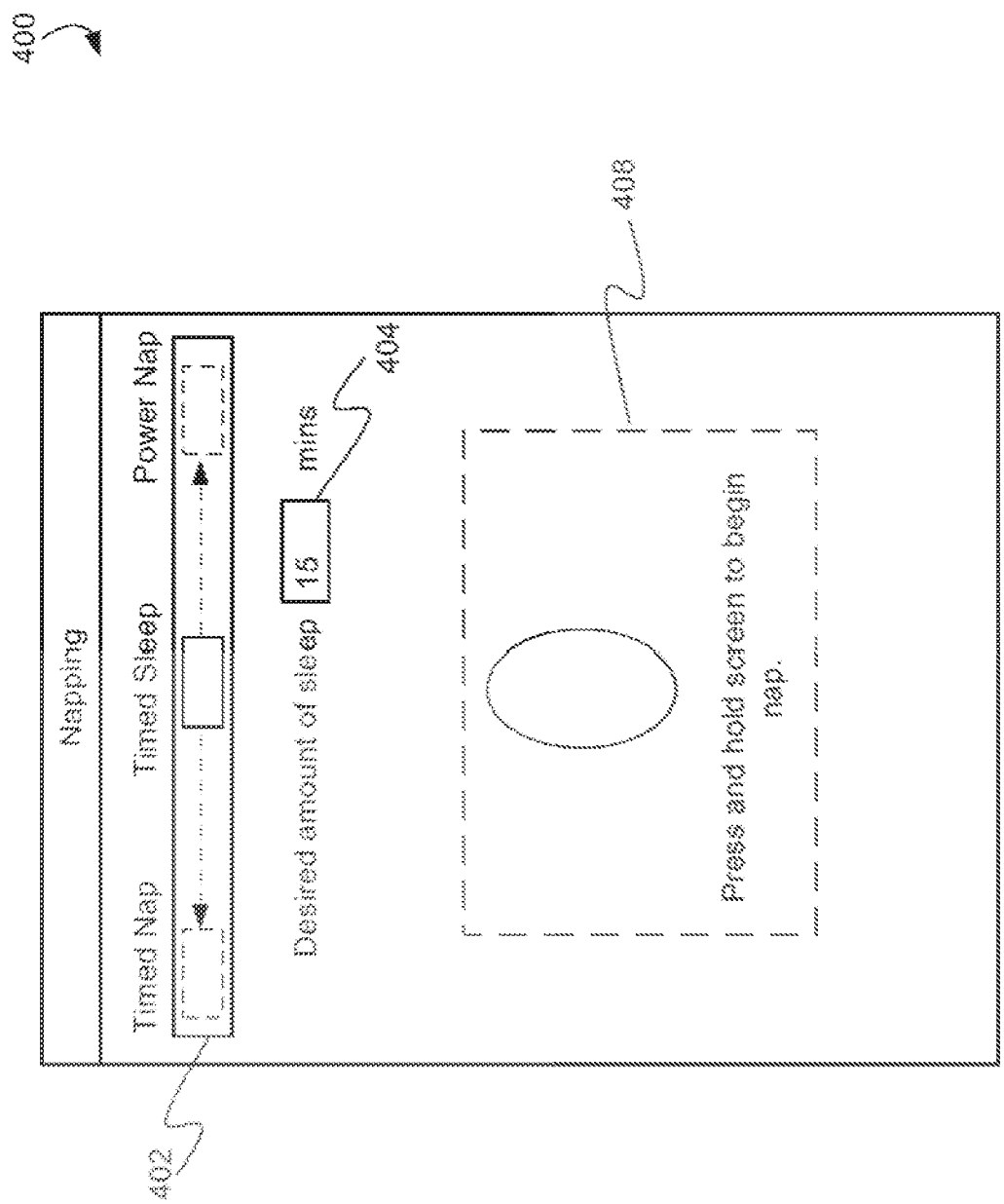
FIG. 4 illustrates an example graphical user interface for determining a sleep onset latency duration based on pressure applied by a user to a display of a computing device.

FIG. 4 illustrates an example graphical user interface 400 for determining a sleep onset latency duration based on pressure applied by a user to a display of a computing device. For example, GUI 400 can be a graphical user interface of sleep application 146 of FIG. 1. GUI 400 can be presented on a display (e.g., touch sensitive display) of computing device 100. GUI 400 can present a user interface for a nap function of sleep application 146, for example. In some implementations. GUI 400 can present graphical element 402. Graphical element 402 (e.g., a nap type selector) can be manipulated (e.g., selected, slid, etc.) by the user to select a type of nap.

In some implementations, the user can select a timed nap function by manipulating graphical element 402. For example, the timed nap function can wake the user with an alarm after a specified period of time. When the timed nap function is selected by the user, the user can enter an amount of time in graphical element 404 (e.g., a text box) to specify an amount of time to nap (e.g., nap window). When the user is ready to nap, the user can press and hold an area of the display of computing device 100 (as indicated by graphical element 408) to begin a nap timer that will sound an alarm after the specified amount of time has elapsed. For example, graphical element 408 can include a prompt requesting that the user apply pressure to an area of the display of computing device 100. When the user is ready to begin sleeping (napping), the user can press and continue to apply pressure to the display. As described above, the display of computing device 100 can include or be backed by a pressure sensor for detecting the amount of pressure applied by a user to the display. When the user initially applies pressure to the display, the napping function can begin the nap timer. When the timer runs down to zero, the napping function can wake the user with an (e.g., audible) alarm.

In some implementations, the timed nap function can determine and display the actual sleep duration. For example, sleep logic 102 can determine the sleep onset latency for the nap period based on the pressure applied to the display of computing device 100, as described above. For example, when the user initially applies pressure to the display, sleep logic 102 can determine that the sleep onset latency period has begun (e.g., the user intends to sleep). When the user releases pressure from the display sleep logic 02 can determine that the sleep onset latency period has ended (e.g., the user has fallen asleep and cannot maintain the pressure on the display). When the alarm sounds after the specified nap period has elapsed, sleep logic 102 can determine that the user is awake. Thus, sleep logic 102 can use the time at which the user initially applied pressure, the time at which the user released pressure, and the time at which the user woke to determine the sleep onset latency duration (e.g., time when pressure released–time when pressure applied) and actual sleep duration (e.g., time when alarm sounded–time when pressure released). When the alarm goes off, sleep application 146 can obtain the sleep onset latency duration and actual sleep duration from sleep logic 102 and present the durations to the user on a GUI 400.

In some implementations, the user can select a timed sleep function by manipulating graphical element 402. For example, when timed sleep is selected, the napping function can automatically adjusting the nap alarm based on sleep onset latency. When the user selects the timed sleep function, the napping function can automatically adjust the nap alarm based on sleep onset latency. For example, when the timed sleep function is selected, the user can specify the amount of time the user wishes to sleep using graphical element 404. For example, sleep logic 102 can determine when the user begins sleeping based on when the user releases pressure from the display of computing device 100, as described above. In response to determining that the user is asleep, sleep application 146 can start a sleep timer that counts down an amount of time corresponding to the amount of sleep specified by the user. For example, if the user specified 15 minutes of sleep, sleep application 146 can start a 15 minute timer when sleep logic 102 detects that the user is asleep. Thus, the user will get the full 15 minutes of sleep that the user desired.

In some implementations, the user can select a power nap function that wakes the user with an alarm when sleep logic 102 determines that the user is entering a deep sleep. For example, the user can manipulate (e.g., select) graphical element 402 to select the power nap function of sleep application 146. When the power nap function is selected, sleep application 146 can request that sleep logic 102 notify sleep application 146 when the user enters a deep sleep. For example, computing device 100 (e.g., a wearable device such as a watch) can detect when the user falls into (or is about to fall into) a deep sleep state. For example, sensors built into computing device 100 can detect the rate and variability of heartbeats and breathing, as described above. Sleep logic 102 can determine that the user has fallen asleep when the heart rate and/or breathing rate fall below a sleep start threshold rate for heart rate or breathing rate. When the user falls into a deep sleep, the user's heartrate and breathing will be reduced even more than initial sleep. Sleep logic 102 can determine that the user has fallen asleep when the heart rate and/or breathing rate fall below a deep sleep threshold rate for heart rate or breathing rate that is lower than the sleep start threshold rate. When sleep logic 102 determines that the user's heart rate and/or breathing rate is near or below the deep sleep threshold rate, sleep logic 102 can notify sleep application 146 and sleep application 146 can sound the alarm to wake the user. Thus, the user will realize the benefit of sleep without the grogginess that is experienced when a user is awakened from a deep sleep.

Figure 5:
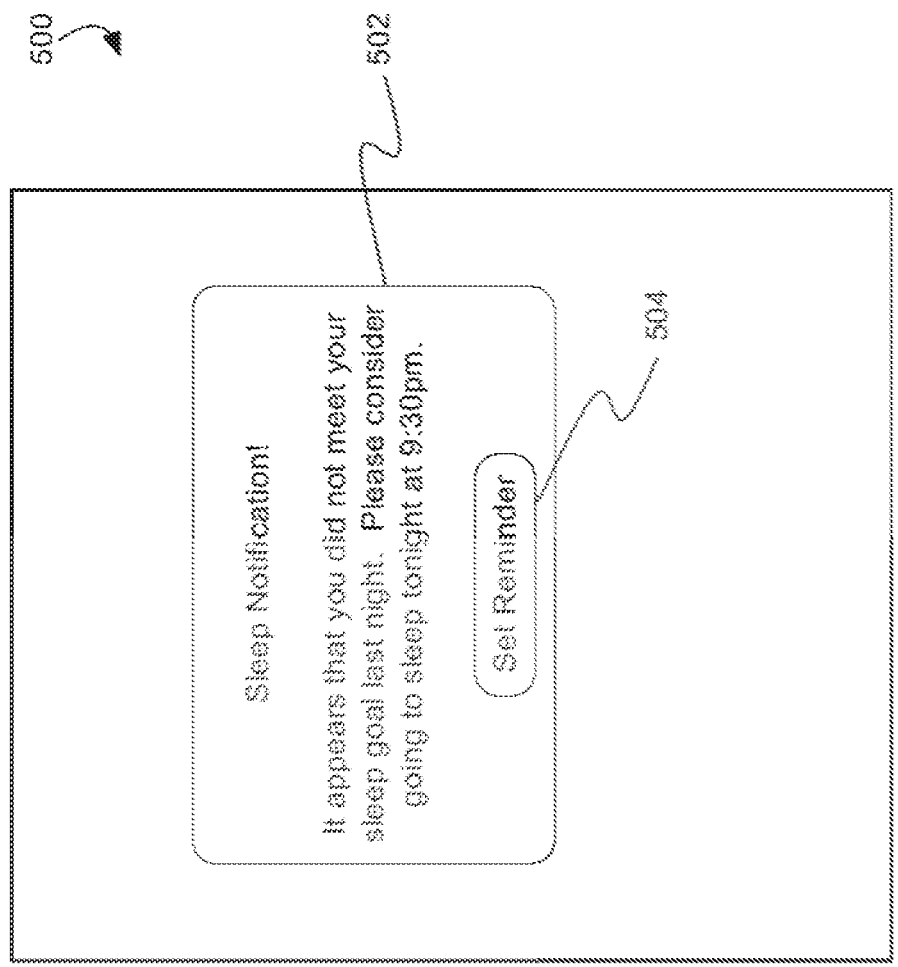
FIG. 5 illustrates an example graphical user interface for suggesting an earlier bedtime to the user.

FIG. 5 illustrates an example graphical user interface 500 for suggesting an earlier bedtime to the user. For example, GUI 500 can be a graphical user interface of computing device 100. In some implementations. GUI 500 can present notification 502 suggesting an earlier bedtime to the user. For example, when sleep logic 102 determines that an alarm should not be adjusted based on the user's sleep onset latency duration because of a conflicting calendar appointment, sleep logic 102 can cause a notification to be presented that suggests an earlier bedtime the following night. Sleep logic 102 can determine the earlier bedtime based on the sleep onset latency duration and/or the user's sleep goal. For example, if the user typically goes to bed at 10 pm and. the sleep onset latency from the previous night was 30 minutes, sleep logic 102 can suggest a bedtime 30 minutes earlier than 10 pm. (e.g., 9:30 pm). If the user typically goes to bed at 10 pm and the sleep deficit (e.g., sleep goal minus actual sleep) from the previous night was 30 minutes, sleep logic 102 can suggest a bedtime 30 minutes earlier than 10 pm (e.g., 9:30 pm).

In some implementations, GUI 500 can include graphical element 504 for configuring a sleep reminder on computing device 100. For example, the user can select graphical element 504 to set sleep reminder for the bedtime (e.g., 9:30 pm) suggested by sleep logic 102. When the user selects graphical element 504 a sleep reminder can be scheduled for the suggested time. When computing device 100 (e.g., sleep logic 102, a reminder application, etc.) determines that the current time is the suggested sleep time, a notification or alarm can be presented by computing device 100 reminding the user to go to bed.

Figure 6:
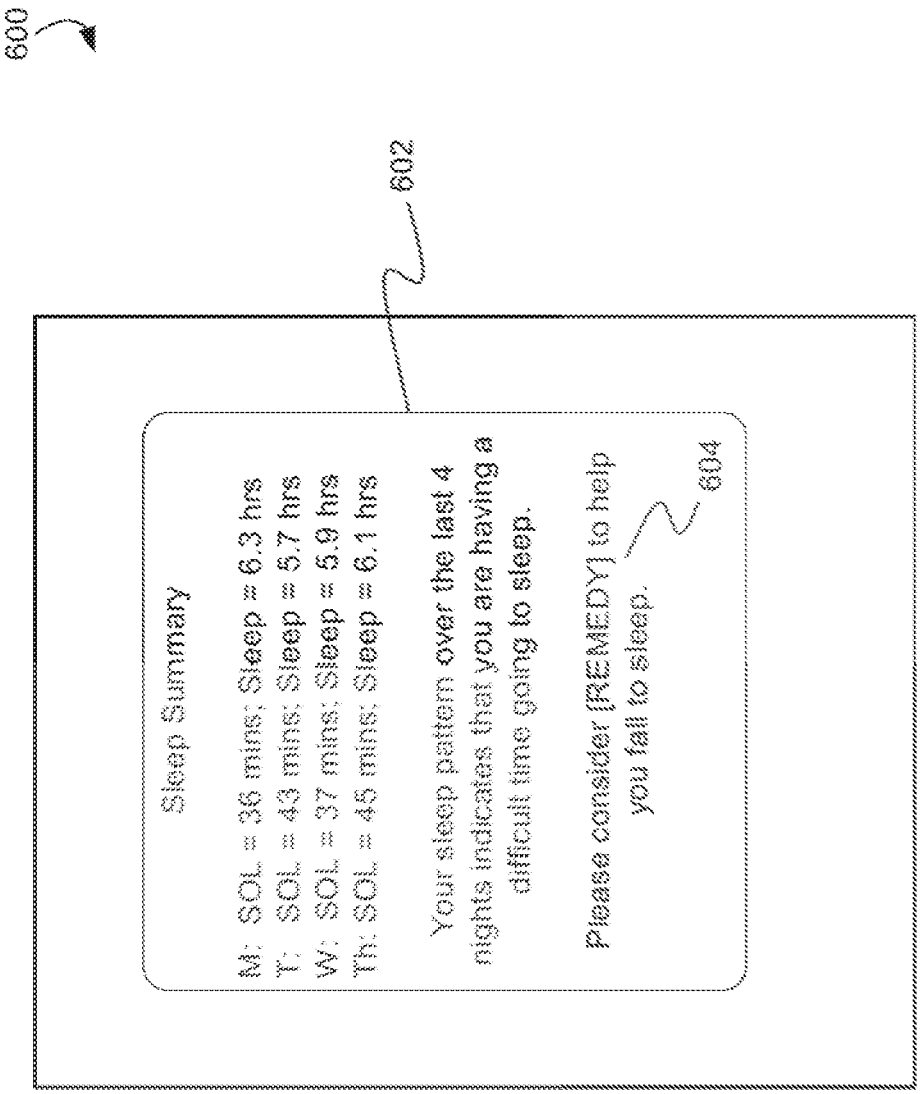
FIG. 6 illustrates an example graphical user interface for presenting a sleep summary indicating a pattern of long sleep onset latency durations.

FIG. 6 illustrates an example graphical user interface 600 for presenting a sleep summary indicating a pattern of long sleep onset latency durations. In some implementations, sleep logic 102 can analyze sleep history data to identify patterns of long sleep onset latency duration. For example, sleep onset latency durations can be categorized as short, normal, and long. A normal sleep onset latency duration can be a duration between a low duration value and a high duration value. A short sleep onset latency duration can be a sleep onset latency duration below the low value (e.g. 5 minutes). A long sleep onset latency duration can be a sleep onset latency duration above the high value (e.g., 25 minutes). In some implementations sleep logic 102 can adjust alarms based on the determined sleep onset latency. However, in some implementations, when the user is experiencing recurring long or short sleep onset latency patterns, sleep logic 102 may not adjust alarms on computing device 100. In some implementations, when the user is experiencing recurring long or short sleep onset latency patterns, sleep logic 102 can present a sleep summary to draw the user's attention to the sleep onset latency patterns.

In some implementations, sleep logic 102 can present notification 602 on GUI 600 when sleep logic detects a pattern of long sleep onset latency. A pattern of long sleep onset latency may indicate that the user is having difficulty falling asleep. For example, when sleep logic 102 identifies a pattern (e.g., over a number of days) of long sleep onset latency durations, sleep logic 102 can present a summary of the user's sleep history using notification 602. Notification 602 can present data representing the sleep onset latency durations and actual sleep durations over the previous number of days, for example.

In some implementations, notification 602 can include a suggestion 604 for activities that the user might perform to improve the user's sleep. For example, suggestion 604 can suggest that the user write her thoughts in a journal, adopt a more consistent routine, go to bed earlier or when feeling fatigued, or speak to a physician about her difficulty falling asleep.

Figure 7:
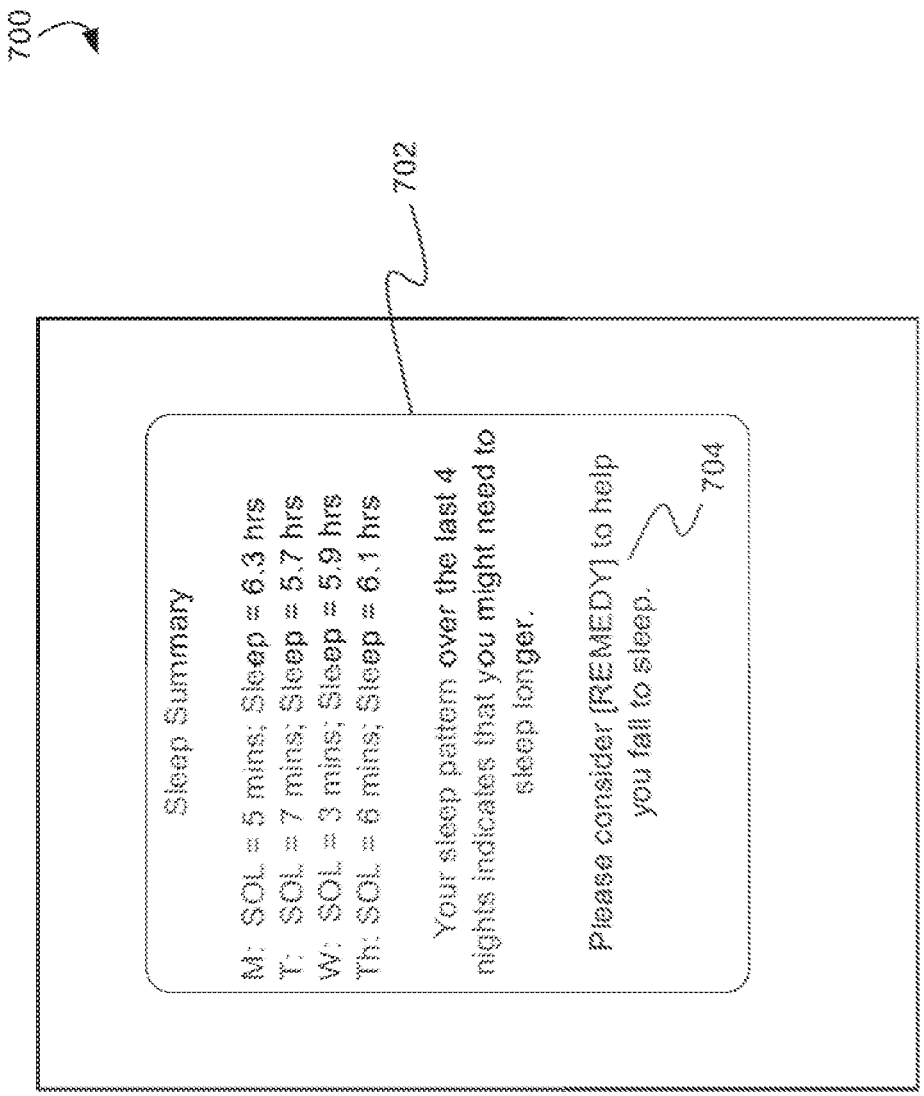
FIG. 7 illustrates an example graphical user interface for presenting a sleep summary indicating a pattern of short sleep onset latency durations.

FIG. 7 illustrates an example graphical user interface 700 for presenting a sleep summary indicating a pattern of short sleep onset latency durations. A pattern of short sleep onset latency durations can indicate that the user is not getting enough sleep. In some implementations, sleep logic 102 can present notification 702 on GUI 600 when sleep logic detects a pattern of short sleep onset latency. For example, when sleep logic 102 identifies a pattern (e.g., over a number of days) of short sleep onset latency durations, sleep logic 102 can present a summary of the user's sleep history using notification 702. Notification 702 can present data representing the sleep onset latency durations and actual sleep durations over the previous number of days, for example.

In some implementations, notification 702 can include a suggestion 704 for activities that the user might perform to improve the user's sleep. For example, suggestion 704 can suggest that the user go to bed earlier, sleep later, lengthen her sleep period, or speak to a physician about her difficulty getting enough asleep.

Example Processes

Figure 8:
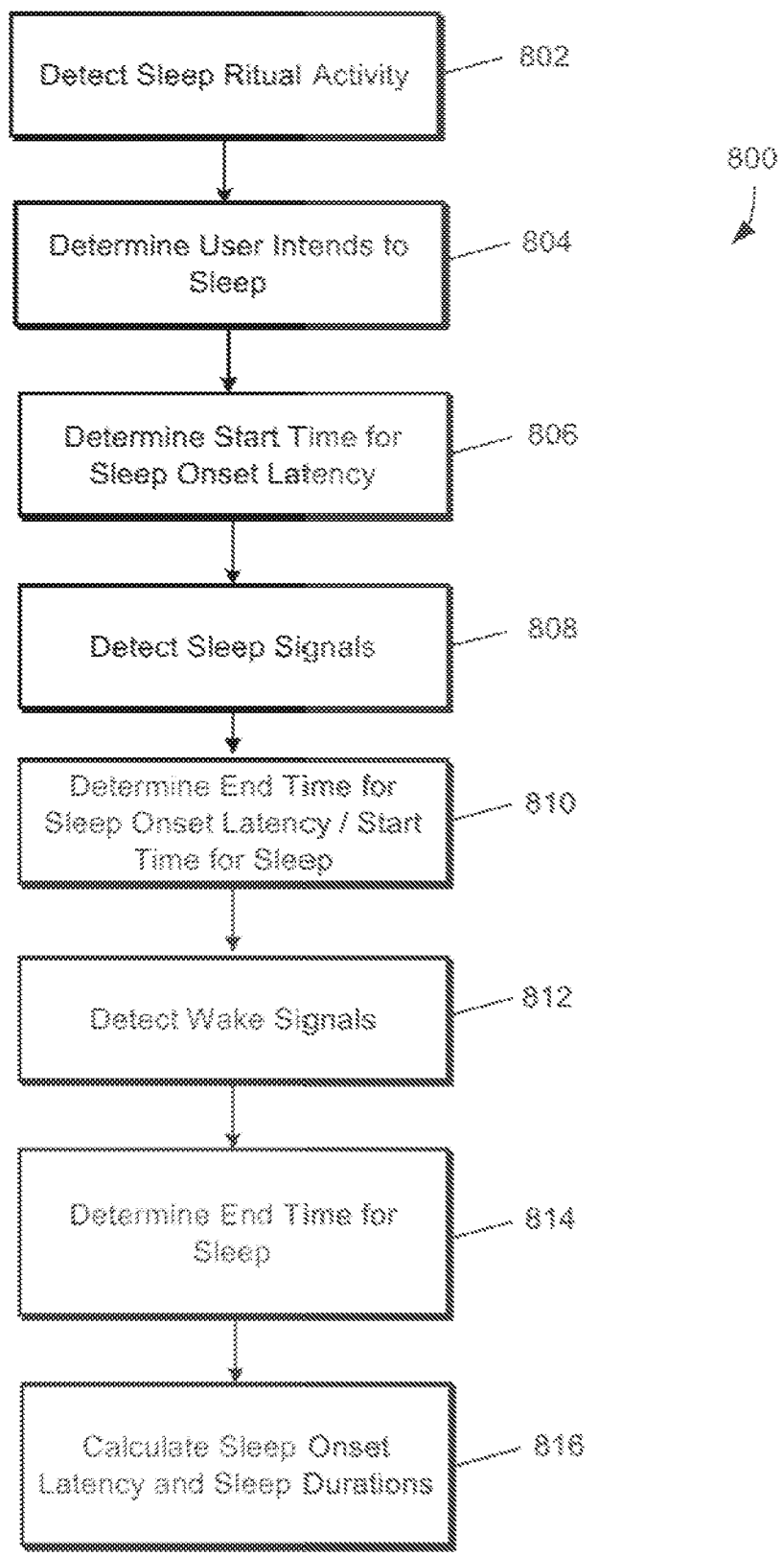
FIG. 8 is flow diagram of an example process for determining sleep onset latency.

FIG. 8 is flow diagram of an example process 800 for determining sleep onset latency. For example, sleep onset latency is a period of time during which the user is trying to go to sleep but has not achieved a sleep state. The beginning of sleep onset latency can correspond to a time when the user intends to sleep. The end of sleep onset latency can correspond to a time when the user falls asleep.

At step 802, computing device 100 can detect a sleep ritual activity. For example, the user may have a ritual of activities that they perform before going to sleep. The user may brush her teeth, run the dishwasher, take a shower, exercise, turn off the bedroom light, lock a door, etc. Computing device 100 can detect these sleep ritual activities according to mechanisms described herein above.

At step 804 computing device 100 can determine that the user intends to sleep. For example, computing device 100 can determine that the user intends to sleep when the user finishes performing the user's sleep ritual, as described above. Computing device 100 can determine that the user intends to sleep based on user input. Computing device 100 can determine that the user intends to sleep based on sensor data (e.g., biometric data) collected by computing device 100, as described above.

At step 806 computing device 100 can determine a start time for the user's sleep onset latency period. For example, the start time can correspond to the time when computing device determines that the user intends to sleep. The start time can correspond to when the last activity of the user's sleep ritual was performed. The start time can correspond to when the last user input was received. The start time can correspond to a time when sensors detected conditions indicative of the user's intent to sleep.

At step 808, computing device 100 can detect sleep signals. For example, sleep signals can include sounds (e.g., snoring, lack of bed noises that reflect the user moving in the bed), biometric data (e.g., heart rate, breathing rate, etc.), and/or lack of user input (e.g., releasing pressure from a pressure sensitive display).

At step 810, computing device 100 can determine an end time for sleep onset latency and/or a start time for sleep. For example, the sleep onset latency period can end when the user falls asleep. The time at which the sleep onset latency period ends and the sleep period begins can correspond to a time when computing device 100 first detected the sleep signals at step 808. Computing device 100 can determine that the user is asleep when computing device 100 detects the sleep signals for a period of time (e.g., 10 minutes).

At step 812, computing device 100 can detect wake signals. For example, wake signals can include user input to computing device 100, movement of computing device 100, sounds corresponding to conscious human activity, and/or other signals indicating that the user is awake.

At step 814, computing device 100 can determine an end time for sleep. For example, the end time for sleep can correspond to a time when computing device 100 first detected the wake signals at step 812. The end time for sleep can correspond to the beginning of a period of conscious user activity. For example, if computing device 100 detects wake signals for a period of time greater than a threshold period of time (e.g., greater than 5 minutes, greater than 10 minutes, etc.), then computing device 100 can determine that the user's sleep period has concluded. By detecting that the user is awake for longer than the threshold period of time, computing device 100 can avoid an erroneous wake determination when the user briefly wakes in the middle of the night to use the restroom or perform some other midnight activity.

At step 816, computing device 100 can calculate a sleep onset latency duration and/or a sleep duration. For example, the sleep onset latency duration can be calculated as the time difference between the start time for sleep onset latency and the end time (e.g., start of sleep) for sleep onset latency. The sleep duration can be calculated as the time difference between the start time for sleep and the end time (e.g., start of sleep) for sleep. In some implementations, the sleep duration can be adjusted based on brief nocturnal wake periods, as described above. Once the sleep onset latency duration and/or the sleep duration are calculated, computing device 100 can store the sleep onset latency duration and/or sleep duration as historical sleep data.

Figure 9:
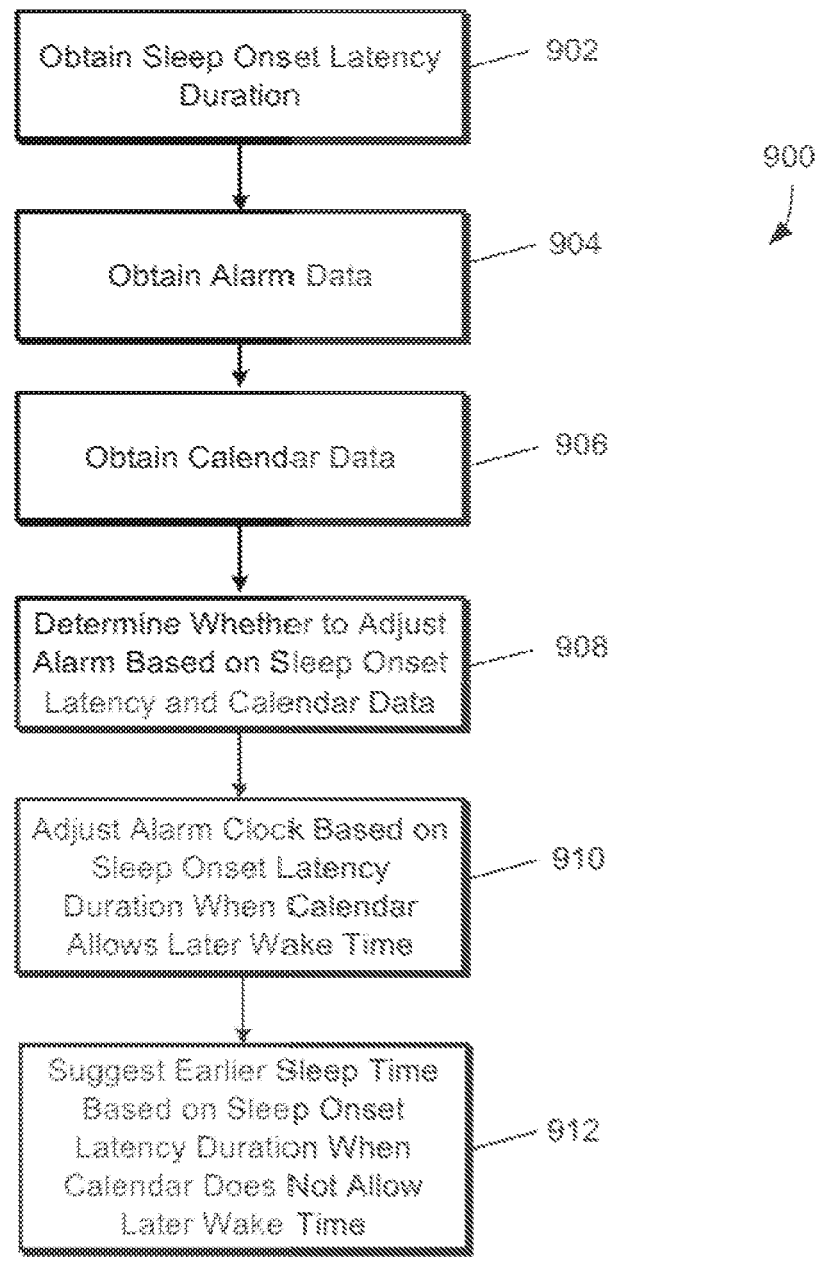
FIG. 9 is a flow diagram of an example process for adjusting alarms based on sleep onset latency.

FIG. 9 is a flow diagram of an example process 900 for adjusting alarms based on sleep onset latency. For example, computing device 100 can adjust an alarm set to wake the user in the morning based on a determined sleep onset latency duration in order to allow the user to get a sufficient amount of sleep.

At step 902, computing device 100 can obtain a sleep onset latency duration. For example, computing device 100 can monitor the user's activities as the user is preparing to sleep and while going to sleep. Computing device 100 can calculate the user's sleep onset latency duration for the current instance of sleep based on the user's activities and other sensor data, as described above.

At step 904, computing device 100 can obtain alarm data. For example, computing device 100 can obtain alarm data from an alarm clock application. Computing device 100 can determine whether an alarm is set to wake the user up in the morning and determine a time at which the alarm is scheduled to wake the user.

At step 906, computing device 100 can obtain calendar data. For example, computing device 100 can obtain calendar data from a calendar application. Computing device 100 can determine whether a calendar event is scheduled in the morning and near the time of the scheduled alarm. When a scheduled calendar event exists, computing device 100 can determine a start time associated with the scheduled calendar event.

At step 908, computing device 100 can determine whether to adjust the scheduled alarm time based on the obtained sleep onset latency and the calendar data. For example, computing device 100 can determine whether adjusting the alarm time to add the sleep onset latency duration to the user's sleep period would cause the user to miss the scheduled calendar event, as described above.

At step 910, computing device 100 can adjust the scheduled alarm time based on the sleep onset latency duration when the scheduled calendar event allows for a later wake time. For example, if the user will still be able to attend the scheduled calendar event after the scheduled alarm time is adjusted, then computing device 100 can adjust the scheduled alarm time based on the sleep onset latency duration to give the user more time to sleep. For example, computing device 100 can add the sleep onset latency duration to the scheduled alarm time to calculate a new alarm time. Computing device 100 can adjust the scheduled alarm time to correspond to the new alarm time. Thus, computing device 100 can help the user get a sufficient amount of sleep and feel well rested.

At step 912, computing device 100 can suggest an earlier sleep time based on the sleep onset latency duration when the calendar data does not allow a later wake time. For example, if adjusting the scheduled alarm time would cause the user to miss the calendar event, computing device 100 can present a notification suggesting that the user go to bed earlier the following night. Thus, computing device 100 can help the user get a sufficient amount of sleep and feel well rested.

Figure 10:
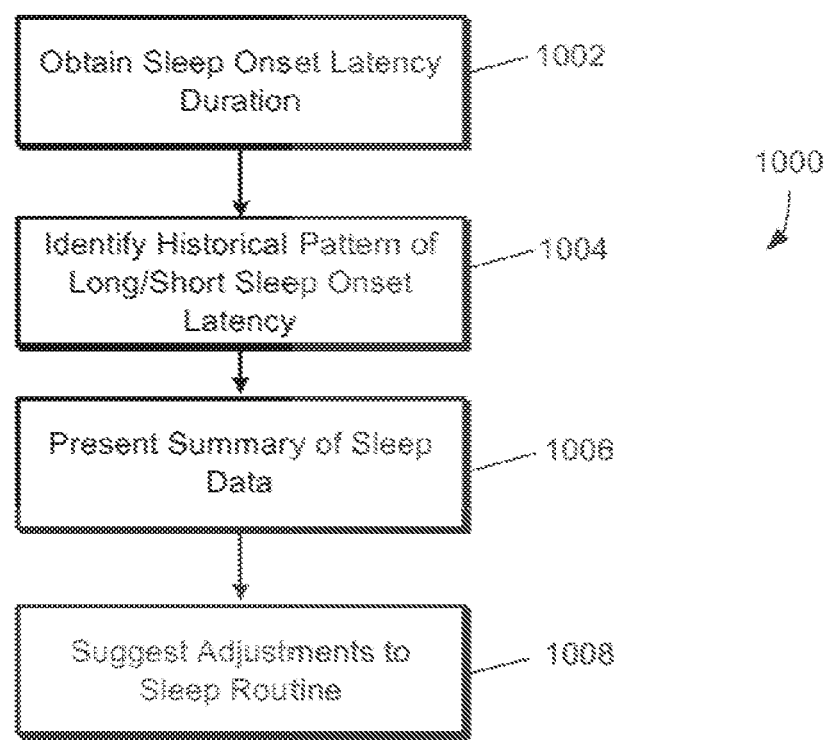
FIG. 10 is a flow diagram of an example process for identifying a pattern of abnormal sleep onset latency.

FIG. 10 is a flow diagram of an example process 10000 for identifying a pattern of abnormal sleep onset latency. For example, sleep onset latency durations can be indicative of a problem sleeping. A recurring pattern of short sleep onset latency can indicate sleep deprivation or exhaustion. A recurring pattern of long sleep onset latency can indicate a mental or physical problem. By presenting information describing a user's sleep onset latency patterns, computing device 100 can draw a user's attention to sleep problems and prompt the user to get help resolving their sleep issues.

At step 1002, computing device 100 can obtain a sleep onset latency duration. For example, computing device 100 can monitor the user's activities as the user is preparing to sleep and while going to sleep. Computing device 100 can calculate the user's sleep onset latency duration for the current instance of sleep based on the user's activities and other sensor data.

At step 1004, computing device 100 can identify a historical pattern of long and/or short sleep onset latency. For example, in response to obtaining the sleep onset latency duration at step 1002, computing device 100 can determine whether the current instance of sleep onset latency is of a short or long duration (e.g., not normal). If the current sleep onset latency duration is short, computing device 100 can analyze the historical sleep data to determine if the user is experiencing a pattern of short sleep onset latency durations. For example, if four out of the last five days of historical sleep data indicate a short sleep onset latency duration, then computing device 100 can determine that the user has a recurring pattern of short sleep onset latency durations. Similarly, if the current sleep onset latency duration is long, computing device 100 can analyze the historical sleep data to determine if the user is experiencing a pattern of long sleep onset latency durations. For example, if three out of the last five days of historical sleep data indicate a long sleep onset latency duration, then computing device 100 can determine that the user has a recurring pattern of long sleep onset latency durations.

At step 1006, computing device 100 can present a summary of sleep data. For example, when computing device 100 identifies a history of long or short sleep onset latency durations, computing device 100 can present a sleep history summary that identifies the sleep onset latency durations and/or the sleep durations for a period of time over which the pattern of short or long sleep onset latency durations occurred.

At step 1008, computing device 100 can suggest adjustments to the user's sleep routine. For example, when computing device 100 identifies a pattern of short sleep onset latency, computing device 100 can suggest that the user get more sleep or adjust the user's sleep goal. When computing device 100 identifies a pattern of long sleep onset latency, computing device 100 can suggest that the user write her thoughts into a journal, adopt a more consistent day to day routine, or speak to a physician. Thus, computing device 100 can draw the user's attention to potential sleep issues in an attempt to help the user sleep better.

Example System Architecture

Figure 11:
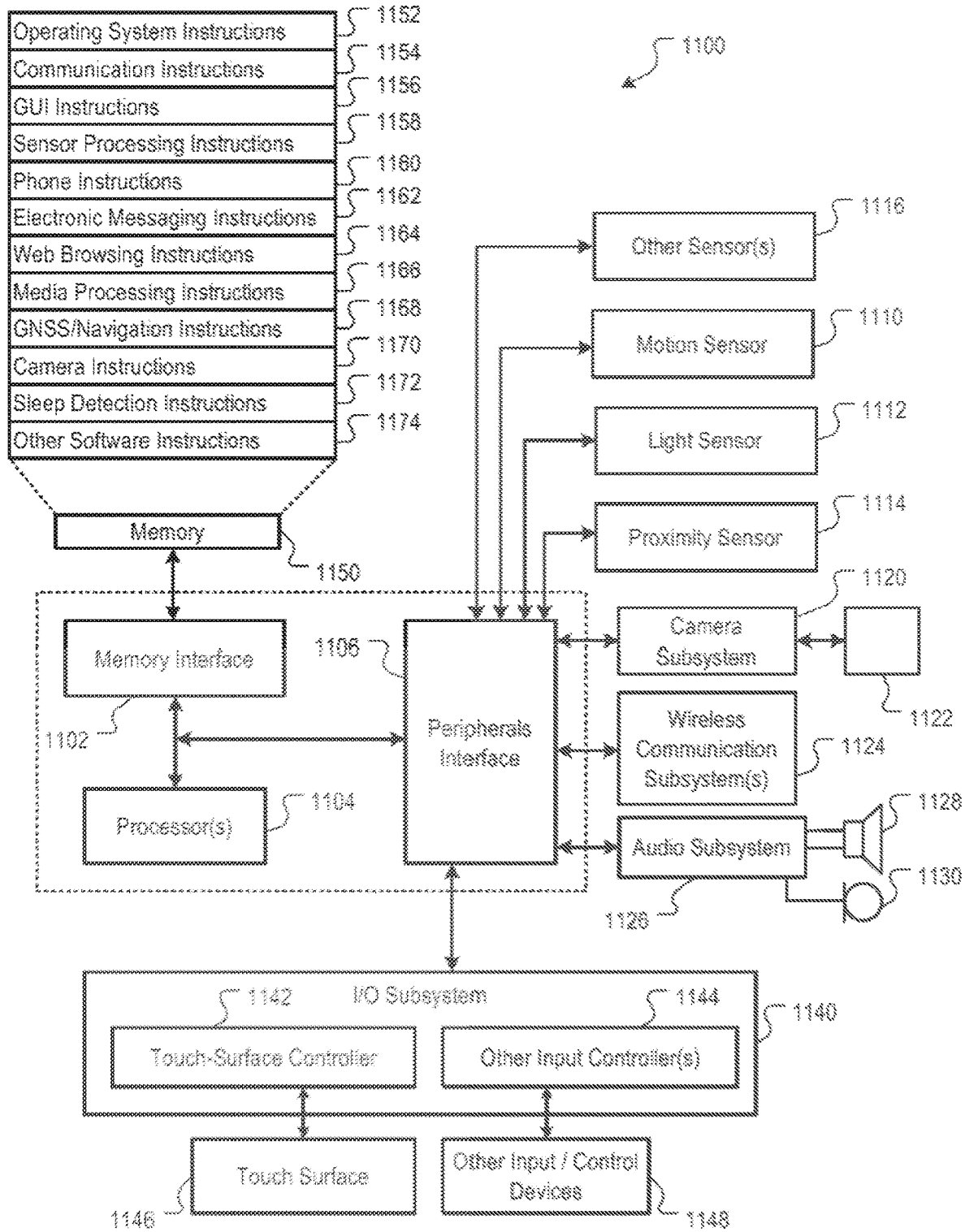
FIG. 11 is a block diagram of an example computing device that can implement the features and processes of FIGS. 1-10.

FIG. 11 is a block diagram of an example computing device 1100 that can implement the features and processes of FIGS. 1-10. The computing device 1100 can include a memory interface 1102, one or more data processors, image processors and/or central processing units 1104, and a peripherals interface 1106. The memory interface 1102, the one or more processors 1104 and/or the peripherals interface 1106 can be separate components or can be integrated in one or more integrated circuits. The various components in the computing device 1100 can be coupled by one or more communication buses or signal lines.

Sensors, devices, and subsystems can be coupled to the peripherals interface 1106 to facilitate multiple functionalities. For example, a motion sensor 1110, a light sensor 1112, and a proximity sensor 1114 can be coupled to the peripherals interface 1106 to facilitate orientation, lighting, and proximity functions. Other sensors 1116 can also be connected to the peripherals interface 1106, such as a global navigation satellite system (GNSS) (e.g., GPS receiver), a temperature sensor, a biometric sensor, magnetometer or other sensing device, to facilitate related functionalities.

A camera subsystem 1120 and an optical sensor 1122, e.g., a charged coupled device (CCD) or a complementary metal-oxide semiconductor (CMOS) optical sensor, can be utilized to facilitate camera functions, such as recording photographs and video clips. The camera subsystem 1120 and the optical sensor 1122 can be used to collect images of a user to be used during authentication of a user, e.g., by performing facial recognition analysis.

Communication functions can be facilitated through one or more wireless communication subsystems 1124, which can include radio frequency receivers and. transmitters and/or optical (e.g., infrared) receivers and transmitters. The specific design and implementation of the communication subsystem 1124 can depend on the communication network (s) over which the computing device 1100 is intended to operate. For example, the computing device 1100 can include communication subsystems 1124 designed to operate over a GSM network, a GPRS network, an EDGE network, a Wi-Fi or WiMax network, and a Bluetooth™ network. In particular, the wireless communication subsystems 1124 can include hosting protocols such that the device 100 can be configured as a base station for other wireless devices.

An audio subsystem 1126 can be coupled to a speaker 1128 and a microphone 1130 to facilitate voice-enabled functions, such as speaker recognition, voice replication, digital recording, and telephony functions. The audio subsystem 1126 can be configured to facilitate processing voice commands, voiceprinting and voice authentication, for example.

The I/O subsystem 1140 can include a touch-surface controller 1142 and/or other input controller(s) 1144. The touch-surface controller 1142 can be coupled to a touch surface 1146. The touch surface 1146 and touch-surface controller 1142 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch surface 1146.

The other input controller(s) 1144 can be coupled to other input/control devices 1148, such as one or more buttons, rocker switches, thumb-wheel, infrared port. USB port, and/or a pointer device such as a stylus. The one or mare buttons (not shown) can include an up/down button for volume control of the speaker 1128 and/or the microphone 1130.

In one implementation, a pressing of the button. for a first duration can disengage a lock of the touch surface 1146; and a pressing of the button for a second duration that is longer than the first duration can turn power to the computing device 1100 on or off. Pressing the button for a third duration can activate a voice control, or voice command, module that enables the user to speak commands into the microphone 1130 to cause the device to execute the spoken command. The user can customize a functionality of one or more of the buttons. The touch surface 1146 can, for example, also be used to implement virtual or soft buttons and/or a keyboard.

In some implementations, the computing device 1100 can present recorded audio and/or video files, such as MP3, AAC, and MPEG files. In some implementations, the computing device 1100 can include the functionality of an MP3 player, such as an iPod™. The computing device 1100 can, therefore, include a 36-pin connector that is compatible with the iPod. Other input/output and control devices can also be used.

The memory interface 1102 can be coupled to memory 1150. The memory 1150 can include high-speed random access memory and/or non-volatile memory, such as one or more magnetic disk storage devices, one or more optical storage devices, and/or flash memory (e.g., NAND, NOR). The memory 1150 can store an operating system 1152, such as Darwin, RTXC, LINUX, UNIX, OS X, WINDOWS, or an embedded operating system such as VxWorks.

The operating system 1152 can include instructions for handling basic system services and for performing hardware dependent tasks. In some implementations, the operating system 1152 can be a kernel (e.g., UNIX kernel). For example, operating system 1152 can implement the sleep onset latency and/or sleep detection features as described with reference to FIGS. 1-10.

The memory 1150 can also store communication instructions 1154 to facilitate communicating with one or more additional devices, one or more computers and/or one or more servers. The memory 1150 can include graphical user interface instructions 1156 to facilitate graphic user interface processing; sensor processing instructions 1158 to facilitate sensor-related processing and functions; phone instructions 1160 to facilitate phone-related processes and functions; electronic messaging instructions 1162 to facilitate electronic-messaging related processes and functions; web browsing instructions 1164 to facilitate web browsing-related processes and functions; media processing instructions 1166 to facilitate media processing-related processes and functions; GNSS/Navigation instructions 1168 to facilitate GNSS and navigation-related processes and instructions; and/or camera instructions 1170 to facilitate camera-related processes and. functions.

The memory 1150 can store other software instructions 1172 to facilitate other processes and functions, such as the sleep onset latency and/or sleep detection processes and functions as described with reference to FIGS. 1-10.

The memory 1150 can also store other software instructions 1174, such as web video instructions to facilitate web video-related processes and functions; and/or web shopping instructions to facilitate web shopping-related processes and functions. In some implementations, the media processing instructions 1166 are divided into audio processing instructions and video processing instructions to facilitate audio processing-related processes and functions and video processing-related processes and functions, respectively.

Each of the above identified instructions and applications can correspond to a set of instructions for performing one or more functions described above. These instructions need not be implemented as separate software programs, procedures, or modules. The memory 1150 can include additional instructions or fewer instructions. Furthermore, various functions of the computing device 1100 can be implemented in. hardware and/or in software including in one or more signal processing and/or application specific integrated circuits.

What is claimed is:

1. A method, comprising:
   receiving, by a computing device, indication of a desired sleep duration;
   calculating, by the computing device, a suggested time for a user to go to sleep based on a scheduled alarm time, an average intended sleep time, the desired sleep duration, and an average sleep onset latency; and
   presenting, by the computing device, a message including the suggested sleep time on a display of the computing device prior to the suggested sleep time.

2. The method of claim 1, further comprising:
   determining, by the computing device over a set of previous days, a daily intended sleep time indicating when the user attempted to go to sleep; and
   determining, by the computing device, the average intended sleep time for the user based on each of the daily intended sleep times over the set of previous days.

3. The method of claim 2, further comprising:
   calculating, by the computing device over the set of previous days, a daily sleep onset latency based on a difference between the daily intended sleep time and a daily actual sleep time; and
   calculating, by the computing device, the average sleep onset latency based on each of the daily sleep onset latencies over the set of previous days.

4. The method of claim 2, further comprising:
   detecting, by the computing device over the set of previous days, pressure applied to a pressure sensor of the computing device at each of the daily intended sleep times; and
   determining, by the computing device over the set of previous days, a reduction in an amount of the pressure applied to the pressure sensor indicating the daily actual sleep time.

5. The method of claim 1, further comprising:
   presenting, by the computing device, a user interface on a display of the computing device; and
   prompting, by the computing device, for entry of the indication of the desired sleep duration.

6. The method of claim 5, further comprising receiving, by the computing device, selection of a sleep timer setting via the user interface, the sleep timer setting being a timed sleep setting which sets an alarm timer to the desired sleep duration without consideration of the average sleep onset latency duration.

7. The method of claim 5, further comprising receiving, by the computing device, selection of a sleep timer setting via the user interface, the sleep timer setting being a timed nap setting which sets an alarm timer to ensure that the desired sleep duration is achieved by considering the average sleep onset latency.

8. A system, comprising:
   one or more processors; and
   a non-transitory computer-readable medium including one or more sequences of instructions that, when executed by the one or more processors, cause:
      receiving, by a computing device, indication of a desired sleep duration;
      calculating, by the computing device, a suggested time for a user to go to sleep based on a scheduled alarm time, an average intended sleep time, the desired sleep duration, and an average sleep onset latency; and presenting, by the computing device, a message including the suggested sleep time on a display of the computing device prior to the suggested sleep time.

9. The system of claim 8, wherein the one or more sequences of instructions further cause:

determining, by the computing device over a set of previous days, a daily intended sleep time indicating when the user attempted to go to sleep; and determining, by the computing device, the average intended sleep time for the user based on each of the daily intended sleep times over the set of previous days.

10. The system of claim 9, wherein the one or more sequences of instructions further cause:

calculating, by the computing device over the set of previous days, a daily sleep onset latency based on a difference between the daily intended sleep time and a daily actual sleep time; and calculating, by the computing device, the average sleep onset latency based on each of the daily sleep onset latencies over the set of previous days.

11. The system of claim 10, wherein the one or more sequences of instructions further cause:

detecting, by the computing device over the set of previous days, pressure applied to a pressure sensor of the computing device at each of the daily intended sleep times; and determining, by the computing device over the set of previous days, a reduction in an amount of the pressure applied to the pressure sensor indicating the daily actual sleep time.

12. The system of claim 8, wherein the one or more sequences of instructions further cause:

presenting, by the computing device, a user interface on a display of the computing device; and prompting, by the computing device, for entry of the indication of the desired sleep duration.

13. The system of claim 12, wherein the one or more sequences of instructions further cause receiving, by the computing device, selection of a sleep timer setting via the user interface, the sleep timer setting being a timed sleep setting which sets an alarm timer to the desired sleep duration without consideration of the average sleep onset latency duration.

14. The system of claim 12, wherein the one or more sequences of instructions further cause receiving, by the computing device, selection of a sleep timer setting via the user interface, the sleep timer setting being a timed nap setting which sets an alarm timer to ensure that the desired sleep duration is achieved by considering the average sleep onset latency.

15. A non-transitory computer-readable medium including one or more sequences of instructions that, when executed by one or more processors, cause:

receiving, by a computing device, indication of a desired sleep duration;

calculating, by the computing device, a suggested time for a user to go to sleep based on a scheduled alarm time, an average intended sleep time, the desired sleep duration, and an average sleep onset latency; and presenting, by the computing device, a message including the suggested sleep time on a display of the computing device prior to the suggested sleep time.

16. The non-transitory computer-readable medium of claim 15, wherein the one or more sequences of instructions further cause:

determining, by the computing device over a set of previous days, a daily intended sleep time indicating when the user attempted to go to sleep; and determining, by the computing device, the average intended sleep time for the user based on each of the daily intended sleep times over the set of previous days.

17. The non-transitory computer-readable medium of claim 16, wherein the one or more sequences of instructions further cause:

calculating, by the computing device over the set of previous days, a daily sleep onset latency based on a difference between the daily intended sleep time and a daily actual sleep time; and calculating, by the computing device, the average sleep onset latency based on each of the daily sleep onset latencies over the set of previous days.

18. The non-transitory computer-readable medium of claim 17, wherein the one or more sequences of instructions further cause:

detecting, by the computing device over the set of previous days, pressure applied to a pressure sensor of the computing device at each of the daily intended sleep times; and determining, by the computing device over the set of previous days, a reduction in an amount of the pressure applied to the pressure sensor indicating the daily actual sleep time.

19. The non-transitory computer-readable medium of claim 15, wherein the one or more sequences of instructions further cause:

presenting, by the computing device, a user interface on a display of the computing device; and prompting, by the computing device, for entry of the indication of the desired sleep duration.

20. The non-transitory computer-readable medium of claim 19, wherein the one or more sequences of instructions further cause receiving, by the computing device, selection of a sleep timer setting via the user interface, the sleep timer setting being a timed sleep setting which sets an alarm timer to the desired sleep duration without consideration of the average sleep onset latency duration.

\* \* \* \* \*